US011446405B1

(12) United States Patent
Qasem

(10) Patent No.: US 11,446,405 B1
(45) Date of Patent: Sep. 20, 2022

(54) SAFE STEADY PORTABLE INCENSE HEATER

(71) Applicant: Sadeq Qasem, Adan (KW)

(72) Inventor: Sadeq Qasem, Adan (KW)

(73) Assignee: Sadeq Qasem, Adan (KW)

( * ) Notice: Subject to any disclaimer, the term of this patent is extended or adjusted under 35 U.S.C. 154(b) by 0 days.

(21) Appl. No.: 17/396,699

(22) Filed: Aug. 8, 2021

(51) Int. Cl.
*A61L 9/03* (2006.01)

(52) U.S. Cl.
CPC ........... *A61L 9/032* (2013.01); *A61L 2209/12* (2013.01); *A61L 2209/135* (2013.01); *A61L 2209/21* (2013.01)

(58) Field of Classification Search
CPC ............................ A61L 9/032; A61L 2209/135
See application file for complete search history.

(56) References Cited

U.S. PATENT DOCUMENTS 10,792,388 B1 * 10/2020 Qasem .................... A61L 9/032

* cited by examiner

*Primary Examiner* — Timothy C Cleveland

(57) ABSTRACT

The present invention generally relates to a safe steady portable incense heater and, more particularly, to a self-contained incense heater shaped as a trapezoid hexagon inflated from bottom for safely holding, igniting, and heating incense (bukhoor wood bricks). The safe steady portable incense heater shaped as a trapezoid hexagon inflated from bottom heats the incense (bukhoor wood bricks) to a specific temperature in order to help the user direct the smoke flow in the exact direction of the nozzle using the fan thrust. The self-contained safe incense heater shaped as a trapezoid hexagon inflated from the bottom has a small hand size and is portable without any wires to enhance the mobility of the users and the way of using incense or bukhoor wood bricks.

5 Claims, 6 Drawing Sheets

SAFE STEADY PORTABLE INCENSE HEATER

DETAILED DESCRIPTION

1. Field of the Invention

The present invention generally relates to a safe, steady portable incense heater and, more particularly, to a self-contained incense heater shaped as a trapezoid hexagon inflated from the bottom for holding safely, igniting, and heating the incense and or the bukhoor wood bricks.

2. Description of the Related Art

Incense burners or heaters are well known and have been in use for many years. Burners or heaters of various designs are appropriate for different applications ranging from religious services to a device for killing flying insects and/or dispensing a pleasant aroma.

For example, a U.S. Pat. No. 9,974,119 of SADEQ relates to a self-contained incense burner shaped as a hairdryer for holding safely, igniting, and burning incense. The portable incense burner shaped as a hairdryer will heat the incense at a specific temperature to help the user direct the smoke flow in the exact direction of the nozzle using the fan thrust. The self-contained incense burner shaped like a hairdryer is small, pocket-size, cordless, and is portable without any wires to ease the mobility of the users and the way of using incense. One of the drawbacks in the said reference is that air will travel in the air duct to the heater chamber directly and through the incense material, resulting in the overheat of the device or the incense material and, therefore, affect the quality of the fragrance.

There are some disadvantages associated with the incense burner; the subject matter of U.S. Pat. No. 9,974,119 such (1) heat time of heating cartridge (a 3D print cartridge) was too slow (>30 seconds), (2) the heating performance of the prior design was not efficient because of the following reasons: the heating cartridge was placed relatively far from the incense (bukhoor) location (outside the incense (bukhoor) tray), and the heater body around the heating cartridge and metal part radiate heat in all directions without concentrating the heat on the incense (bukhoor) itself, (3) the heating cartridge is placed close to the printed circuit board (PCB) which creates a risk of damaging the PCB by heat, (4) the incense (bukhoor) could move around the metal part and thereby reduce the heating efficiency substantially, and (5) the metal part and heating cartridge were not well insulated which cerate the risk of damaging casing parts by heat.

Another prior art reference is U.S. Pat. No. 10,792,388, issued on Oct. 6, 2020, in the name of Sadeq A. Qasem. The said reference discloses a reversed (L) shaped safe portable incense heater comprising a hollow housing body with horizontal housing attached to a vertical housing. The claimed device is a portable one.

Notwithstanding the above, it is presently believed that there is a potential demand and a commercial market for an incense heater and storage device in accordance with the present invention, especially for use in offices, clothing cabinets, cup-holders in cars, and suitable for hotel rooms While the present invention is portable and can be carried by hand, one of its main features is that it is steady and can be used in the mentioned places.

SUMMARY OF THE INVENTION

The present invention generally relates to a safe, steady portable incense heater and, more particularly, to a self-contained incense heater shaped as a trapezoid hexagon inflated from the bottom for safely holding, igniting, and heating incense or and the bukhoor wood bricks.

The safe, steady portable incense heater shaped as a trapezoid hexagon inflated from the bottom specific will heat the incense or bukhoor wood inside it at a particular temperature to allow the user to place the smoke flow exact location using the fan thrust. The self-contained incense heater shaped as a trapezoid hexagon inflated from the bottom is small, hand-size, portable, and without any wires to enhance the mobility of the users and the way of using incense or bukhoor wood bricks.

When the device is operated, it sprinkles the fragrance, the incense of wood heating (bukhoor), and the user can use it or apply the fragrant mist on his body, clothes, hair, car, and house, or even any place.

These and other features will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
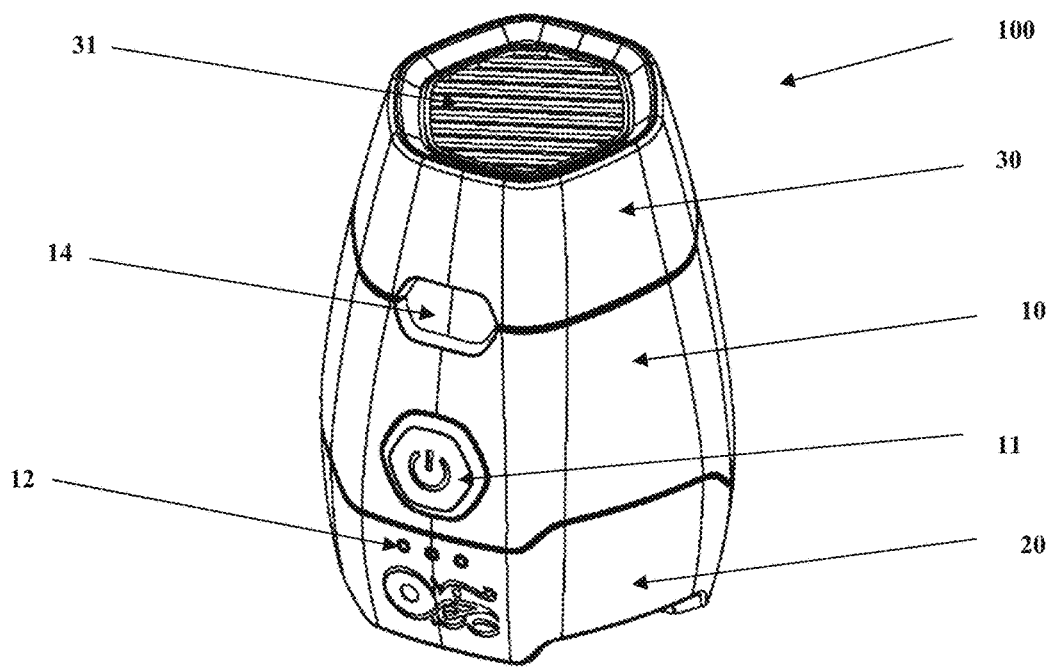
FIG. 1 is an exterior side perspective view of the safe, steady portable incense heater showing the outlet cap closed.
Figure 2:
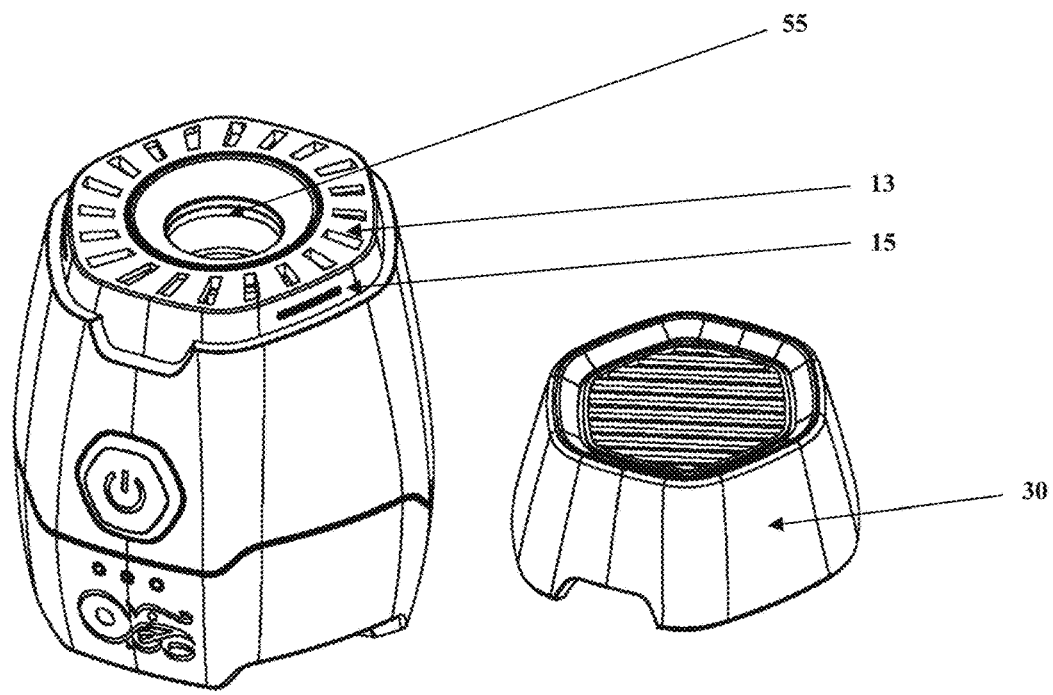
FIG. 2 is an exterior side perspective view of the safe, steady portable incense heater shown when the outlet cap is opened.
Figure 3:
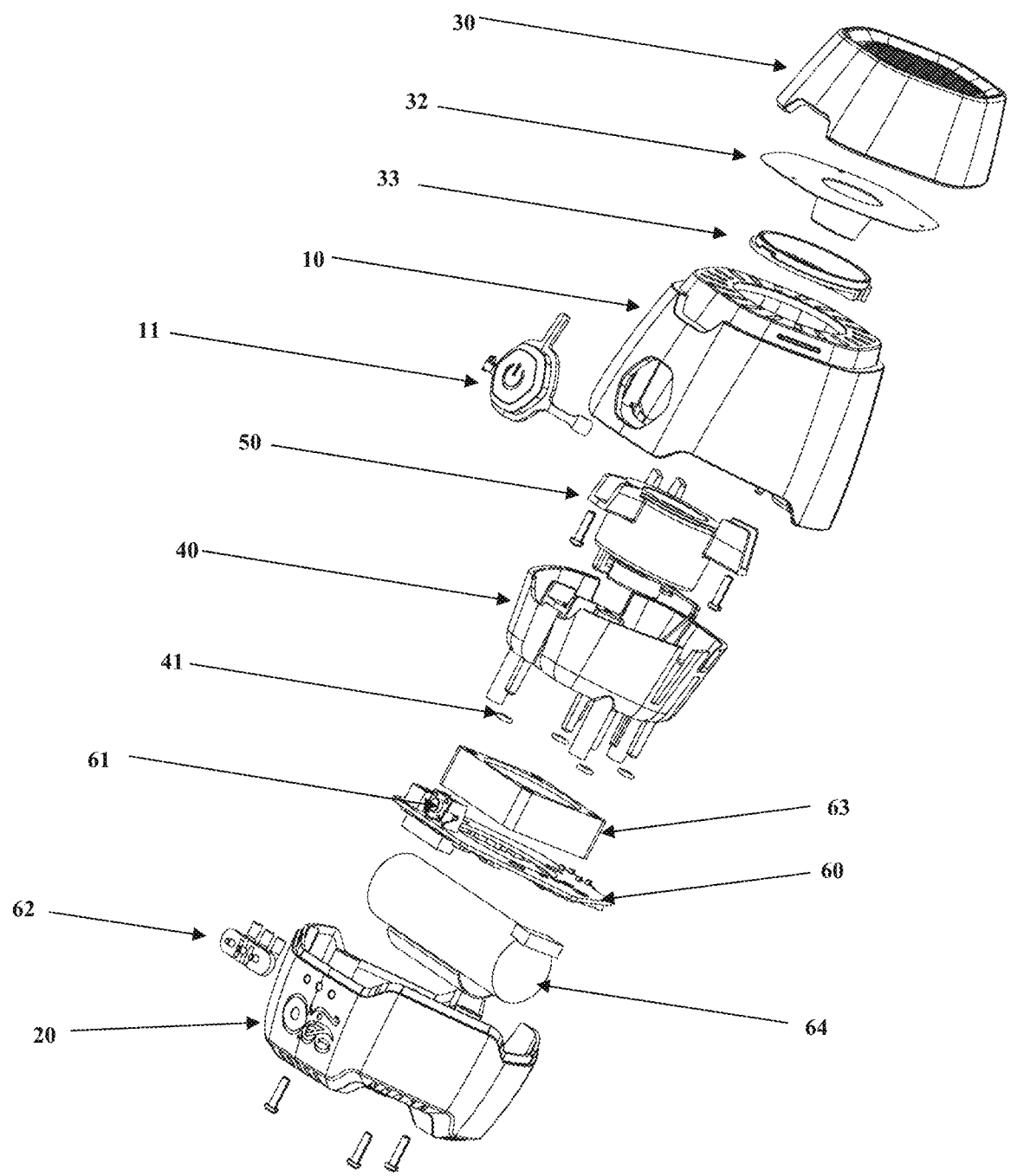
FIG. 3 is a detailed part exploded view of a safe, steady portable incense heater.

FIGS. 1, 2, and 3 describe an outside perspective view of the safe, steady portable incense heater 100 with cap closed, opened, and detailed parts. The safe, steady portable incense heater 100 comprises a hollow housing body shaped as a trapezoid hexagon inflated from the bottom, having a middle main housing 10 attached to bottom housing 20. The middle main housing 10 has a curved bottom end mounted with the bottom housing 20. On the top of the middle main housing 10, there is a cap groove 14, which is aligned and connected to cap 30, the cap groove 14 used to open the cap 30 in the present invention, the cap 30 has an outlet cap grill 31 wherein the incense fragrance smoke pushed out as an exhaust air 300 to the desired areas since the natural flow of the smoke is against gravity and with the help of the thrust power of the air which generated by the fan 63.

The middle main housing 10 comprises the main switch 11 and LED indication surface 12, both connected from behind the middle main housing 10 with the electronic printed circuit board (PCB 60). The three LED 62 are located exactly behind LED indication surface 12 on the main middle housing 10, so the users can see the status of the incense heater. Also, the trigger on-off button 61 in the circuit board 60 is located exactly and connected to the main switch 11 in the middle main housing 10.

In the FIGS. 2, 3, 6, 8 and 9, the Fan 63 is mounted on the middle inner side of middle main housing 20, exactly on top the circuit board 60 and below air duct guide 40, also its in line with the air inlet vent 21, the fresh air 200 will be sucked through the air inlet vent 21 and it will be driven through the air duct guide 40, which is mounted on the top side of the fan 63, silicon rubber rings 41 are placed between the fan 63 and the air duct guide 40 to prevent parts vibration inside the present invention, the air will go around the heater housing 50 and goes through the air outlet vent 13 on the middle main housing 10 with high speed, a suction force will be generated inside the heating chamber 55, the heating chamber 55 is the place where the users put their incense material, using the physics of suction force which is generated by the air traveling inside the present invention, the air will carry the fragrance smoke from inside the heating chamber 55 to the outlet cap grill 31 spreading the incense fragrance smoke with high speed air 300 outside to the users, the inventive step of the present invention is forming suction force inside the heating chamber 55 were the wood bricks 70 placed, which generated by internal high speed air traveling 71 around the heating element housing 50 to drive the incense fragrance smoke to the outlet cap grill 31, the internal high speed air traveling 71 will create suction force inside the heating chamber 55 and will carry the incense fragrance 72 into the outlet cap grill 31 as a high speed air 300 outside to the users and this way is better than blow air into the incense or wood bricks which will affect the quality of the incense fragrance itself, also when the air will go around the heater housing 50 it will cooldown the parts around the heater and make sure that the present invention will not be over heated nor heating reaches the main middle housing 10 were the users holds with their hands.

In FIGS. 1, 3, 7, and 10, cap 30 comprises of an outlet cap grill 31 where the high-speed fragrance air 300 spreads out to the users, cap groove 14 help the users easily grabbing the cap and open it in order to place the incense material in the heating chamber 55, from the inner side of the cap 30, metal sheet 32 is mounted inside the cap 30 by silicon rubber frame 33, the uses of the metal sheet 32 is to prevent the incense material from moving from inside the heating chamber 55 and to guide the incense 72 to the outlet cap grill 31 spots without mixing the incense with high internal speed traveling 71 so it will not lose its incense quality smell.

Figure 6:
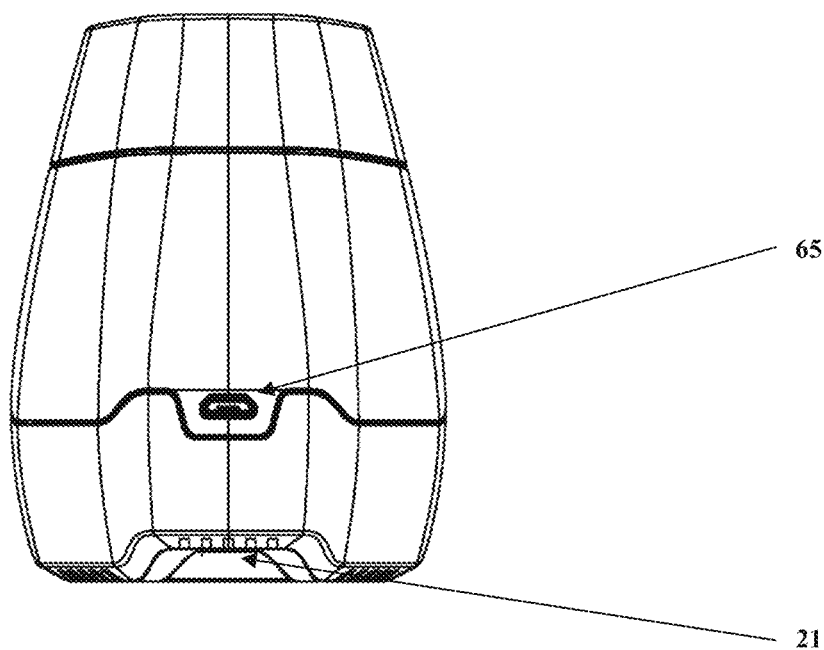
FIG. 6 is a perspective view of the present invention from the backside, showing the USB charging port.
Figure 7:
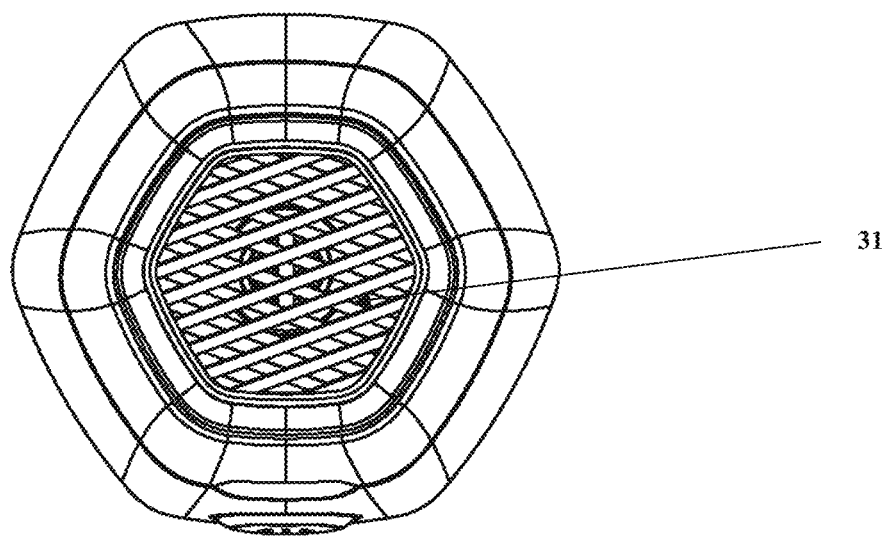
FIG. 7 is a perspective view from the top side of the safe, steady portable incense heater showing the outlet cap and outlet grill.
Figure 8:
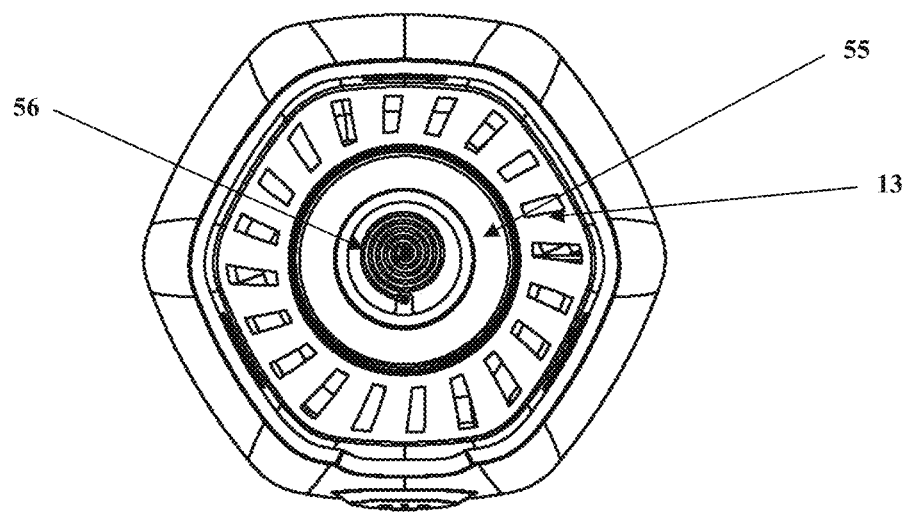
FIG. 8 is a perspective view from the top side of the safe, steady portable incense heater without outlet cap showing bukhoor chamber and heating coil.
Figure 9:
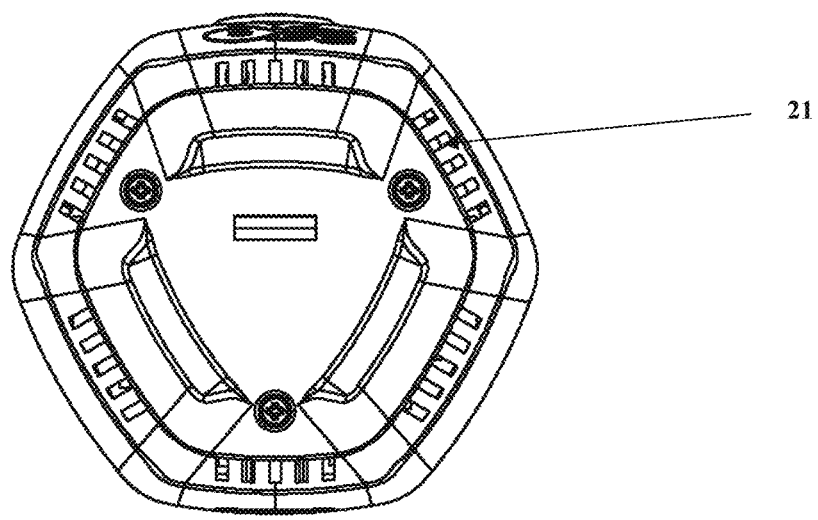
FIG. 9 is a perspective view from the bottom side of the safe, steady portable incense heater showing an inlet vent.
Figure 10:
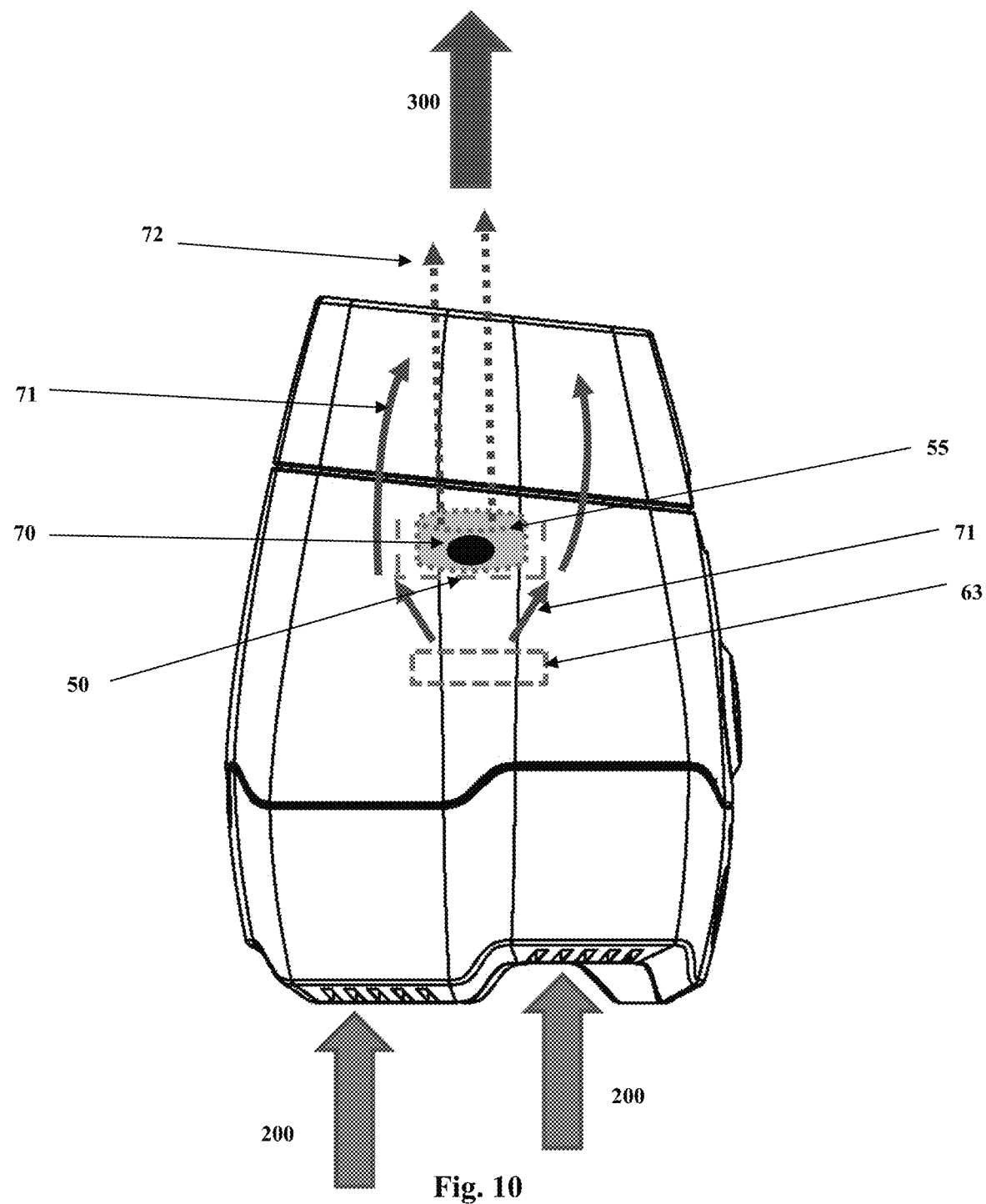
FIG. 10 is a perspective view of the safe, steady portable incense heater operation showing airflow direction.

In FIGS. 3 and 6, the electronic circuit board 60 is placed in the inner of middle main housing 10, and it is mounted on top of battery 64. On the backside of circuit board 60, there is USB port 65 that appeared in the backside of the middle main housing 10, which through it the users can recharge the battery 64 through the USB port 65.

Figure 4:
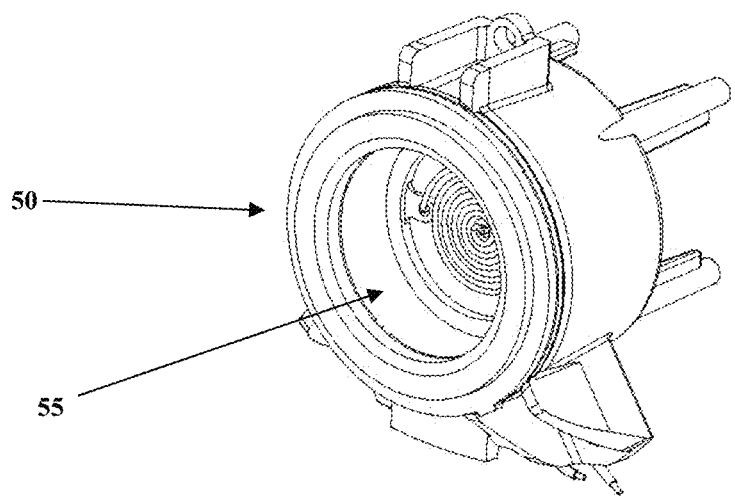
FIG. 4 is a perspective view of the heater housing and bukhoor chamber.
Figure 5:
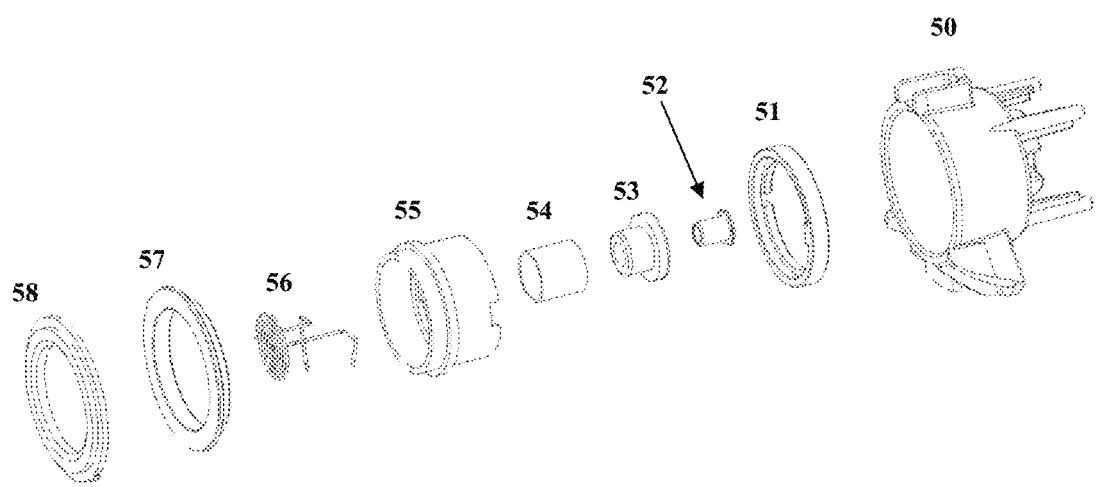
FIG. 5 is a detailed exploded view of the heater housing and bukhoor chamber.

In FIGS. 3, 4, and 5, the heating housing 50 comprises of inner O-ring 51, which holds the heating chamber 55 inside the heating housing 50, heating coil 56 is placed inside the heating chamber 55, inner ceramic 52, outer ceramic 54, and middle silicon rubber 53 mounted behind the heating coil 56 to secure heating coil 56 wires and to prevent short circuits in the present invention, the outer O-ring 57 and circular housing frame 58 is placed respectively on the other side of the heating housing 50 to secure the heating chamber 55 from shaking while using the present invention by the users, the benefits from inner O-ring 51 and outer O-ring 57 is to prevent heats from spreading to the other parts of the present invention and is also to secure the heating chamber in its place inside the heating housing 50.

In FIGS. 3, 4, and 5, heating coil 56, electronic USB port 65, fan 63, and battery 64 are connected to the electronic circuit board 60 by soldering pins wires. Main switch 11 connected to the electronic circuit board 60 mechanically on the trigger on-off button 61, which soldered in the electronic circuit board 60.

It is to be understood that the present invention is not limited to the embodiments described above but encompasses any and all embodiments within the scope of the following claims.

The invention claimed is:

1. An incense heater comprising:
   a hollow housing body having a substantially hexagonal cross-section, wherein the hollow housing comprises a middle main housing and a bottom housing, and a curved bottom end of the middle main housing is configured to be attached to a curved top end of the bottom housing;
   a cap having an outlet cap grill and detachably mounted on a top end of the middle main housing, wherein a first cap groove is provided in the top end of the middle main housing, and a second cap groove is provided in a bottom end of the cap, and when the cap is mounted on the top end of the middle main housing, and the second cap groove is aligned and connected to the first cap groove to form a cap groove for opening the cap;
   a heating housing provided within the middle main housing, the heating housing comprising a heating chamber and a heating coil, wherein the heating chamber is provided in the heating housing and is configured to accommodate an incense material, and the heating coil is provided in the heating chamber and is configured to heat the incense material to generate incense fragrance smokes;
   a fan mounted on a middle inner side of the middle main housing and configured to generate a thrust power of air, wherein due to a natural flow of the incense fragrance smokes being against gravity and with help of the thrust power of air, the incense fragrance smoke is pushed out as a high-speed air to desired areas.

2. The incense heater according to claim 1, wherein the middle main housing comprises a main switch and an LED indication surface, both connected from behind the middle main housing with an electronic printed circuit board (PCB), three LEDs are located exactly behind the LED indication surface on the middle main housing, a trigger on-off button in the electronic printed circuit board is located exactly and connected to the main switch in the middle main housing.

3. The incense heater according to claim 2, wherein the cap has a hexagonal cross-section, and perimeters of hexagonal cross-sections gradually decrease from a bottom of the cap to a top of the cap.

4. The incense heater according to claim 2, further comprising a USB port and a rechargeable battery, wherein the USB port is provided in a backside of the middle main housing, and the rechargeable battery is charged through the USB port.

5. The incense heater according to claim 3, wherein the heating housing further comprises:
   a first O-ring, which holds the heating chamber inside the heating housing;

a first ceramic, a second ceramic, and a middle silicon rubber, wherein the inner ceramic, the outer ceramic, and the middle silicon rubber are mounted behind the heating coil to secure the heating coil and to prevent short circuits; and a second O-ring and a circular housing frame, wherein the second O-ring and the circular housing frame are covered on a side of the heating housing to secure the heating chamber from shaking during use, the first O-ring and the second O-ring are configured to prevent heats from spreading to the other parts of the incense heater and to secure the heating chamber in its place inside the heating housing.

\* \* \* \* \*